United States Patent [19]

Szot

[11] 4,024,405
[45] May 17, 1977

[54] X-RAY EYE SHIELD

[76] Inventor: Frank A. Szot, 630 Fountainhead Way, Naples, Fla. 33940

[22] Filed: Dec. 4, 1975

[21] Appl. No.: 637,765

[52] U.S. Cl. .................................. 250/516; 2/2; 2/15
[51] Int. Cl.² ........................................ G21F 3/00
[58] Field of Search .................... 250/515, 516, 250/519; 2/2, 14 R, 14 H, 15

[56] References Cited

UNITED STATES PATENTS

| 589,307 | 8/1897 | Seffer | 2/15 |
| 2,874,385 | 2/1959 | Wade | 2/15 |
| 3,020,552 | 2/1962 | Coon | 2/15 |

Primary Examiner—Archie R. Borchelt
Attorney, Agent, or Firm—Biebel, French & Nauman

[57] ABSTRACT

An X-ray eye shield useful in protecting eye tissue from radiation during dental radiography. The eye shield has a radiolucent frame and radiopaque lens cups which prevent passage of X-ray radiation.

5 Claims, 5 Drawing Figures

U.S. Patent   May 17, 1977   4,024,405
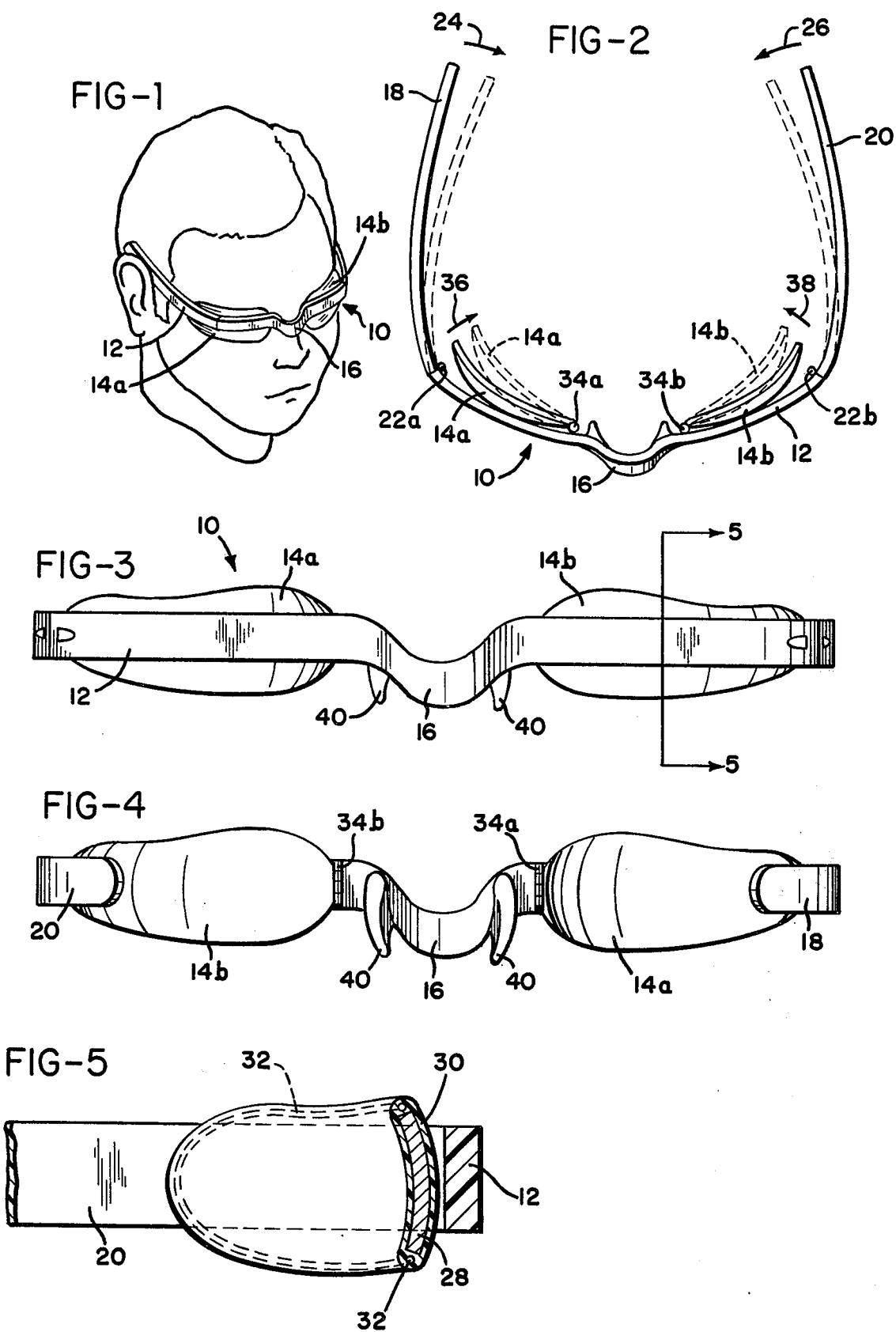

X-RAY EYE SHIELD

BACKGROUND OF THE INVENTION

This invention relates to a dental X-ray eye shield and more particularly to a glasses-type of shield having a radiolucent frame and radiopaque, shielding lens cups.

The public is exposed daily to possible radiation from the following sources: medical and dental X-rays, the sun, color television, microwave ovens, etc. According to the U.S. Public Health Service, the two greatest sources of exposure are medical and dental X-rays.

In the field of dentistry, radiographs have become a standard diagnostic procedure. However, this is of concern to many since unnecessary exposure to radiation is thought to be harmful. Not only is radiation of concern during routine dental X-rays, but it is especially important when a series of radiographs are required, e.g., in the diagnosis and evaluation of so many potential young orthodontic patients.

For these reasons, Medwedeff in U.S. Pats. Re. Nos. 25,773; 3,092,721, and 3,304,423 addresses the problem. Disclosed in the Medwedeff patents is a dental X-ray shield and aiming means. The Medwedeff device is an attempt to prevent any unnecessary radiation exposure. While this is certainly a laudable objective, the system of Medwedeff is cumbersome, difficult to use, and has found little acceptance in the profession. Therefore, the problem remains.

At present, the only readily accepted solution is use of blanket or garment type shields containing lead impregnated plastic materials. These are conventionally draped over the patent's chest during dental radiography. They do not protect the eyes.

One thought is that the eyes alone might be protected easily and economically without resorting to a Medwedeff-type device. This is an area of particular concern since the tissues of the eye are very susceptible to radiation. Cataracts and tumors of the eye may result from accumulated excessive radiation.

Of course, eye radiation shields are known, but to my knowledge none have been used as a protection against dental X-rays. In fact, the eye radiation shields with which I am familiar could not be used effectively for that purpose. That is, Crosson (U.S. Pat. No. 3,030,628 ) and Christianson (U.S. Pat. No. 3,325,825 ) shown eye radiation shields, but neither would effectively block out X-ray radiation from all angles. Christianson is an RF radiation shield in the form of goggles. It has a conductive frame and a light transparent lens. The conductive frame would also make it unacceptable for dental use. It would be impossible to position the X-ray machine cone for quality radiographs on a patient wearing such an eye shield because important anatomical landmarks vital to an accurate diagnosis would be blocked or distorted by the conductive frame. Besides an RF radiation shield which permits vision through the lenses, would not effectively protect the eyes themselves against X-ray radiation.

The mask of Crosson is similar. The louvers 21 of Crosson protect against radioactive radiation, but at the same time allow vision through the lens.

Accordingly, the need remains for an eye shield which may be used during dental radiography without interference of the frame in making the radiographs while at the same time preventing radiation exposure of the eye tissue.

SUMMARY OF THE INVENTION

The present invention fulfills that need by providing an X-ray eye shield which will effectively protect the patient's eye tissue without interfering in any manner with the work of the dentist, hygienist, or dental assistant. It will protect against excess radiation during routine diagnostic radiographs, as well as provide a safety shield to protect the eyes from any radiation leaks which might occur. Perhaps more significantly, it will help allay the fear and apprehension of so many radiophobic patients who are concerned about the potential dangers of radiation.

The eye shield of the instant invention is basically a glasses-type device which fits the head of the patient. A radiolucent frame (plastic) conforms to the contour of the head. Spring-loaded hinges may be used to hold the frame tightly in place on the patient. The bridge of the frame is lower than on a normal spectacle frame. This permits positioning of the nose guide of certain common X-ray machines on the bridge of the nose.

Attached to the frame are two radiopaque lens cups. These are hinged passively so that they may be adjusted, as desired, into close conformity with the eye socket. The lens cups contain a material which will prevent passage of X-ray radiation. In this case the material is preferably 0.030 to 0.040 inch thick lead encased in plastic. A suitable thin metal support or frame may be used for support of the lens cups, although, this is not necessary.

The lens cups are coextensive with the metal hinges on the frame so that the only areas from which radiation is occluded is the area inside the eye socket. All other surrounding areas of the oral cavity are exposed so that the important anatomical landmarks necessary to accurate diagnosis may be X-rayed without distortion.

Accordingly, it is a object of the present invention to provide an X-ray eye shield which may be used during dental radiography.

Other objects and advantages of the invention will be apparent from the following descripton, the accompanying drawing and the appended claims.

BRIEF DESCRIPTON OF THE DRAWING

FIG. 1 is a perspective view of the X-ray eye shield of the present invention positioned on the head of the patient;

FIG. 2 is a top plan view of the X-ray eye shield;

FIG. 3 is an elevational view of the X-ray eye shield from the front;

FIG. 4 is an elevational view of the X-ray eye shield from the back; and

FIG. 5 is a cross-section along the lines 5—5 of FIG. 3.

DESCRIPTION OF THE PREFERRED EMBODIMENT

Referring to FIG. 1, there is shown an X-ray eye shield 10 in place on the head of a patient. As can be seen, the eye shield 10 with frame 12 closely fits the contours of the head and radiopaque lens cups 14a and 14b fit comfortably against the eye socket. The lens cups 14a and 14b shield the opening of the eye socket from all angles.

FIGS. 2–4 show eye shield 10 in more detail. Thus, it is seen to have a frame 12 with a bridge portion 16 and temple pieces 18 and 20. These three parts are attached at hinges 22a and 22b. The hinges 22a and 22b may be spring-loaded so that the temple pieces 18 and 20 are biased against the temples as shown by directional arrows 24 and 26. Other arrangements to obtain a close fit may also be used.

Frame 12 is made of a radiolucent plastic material of any type commonly used in spectacle frames. However hinges 22a and 22b are metal and would distort a radiopgraph taken in the area over which the hinges are positioned. Therefore, it is desirable to have hinges 22a and 22b coextensive with lens cups 14a and 14b so that only the sensitive eye area is blocked from X-ray radiation. Likewise, no metal reinforcement as commonly found in spectacle frames in used.

Lens cups 14a ad 14b are made of a material which will prevent passage of X-ray radiation. Typical of such materials is lead film encased in a plastic material, for example, a 0.030 – 0.040 inch or more thickness lead film. Other materials which prevent the passage of X-ray radiation could also be used. The structure of the preferred laminated lens cup is best shown in FIG. 5. There lead film 28 is surrounded by plastic 30, which may be ABS, acrylic, vinyl, polyamide or other known rigid plastics. For support a thin metal wire or rod 32 is located around the periphery of the lens cups, although this is not necessary if the plastic material is strong enough to have the hinges embedded therein without the need for further support. Similarly, an exterior frame could be used rather than a embedded wire.

In any event, lens cup 14a and 14b are attached via the plastic (reinforced or not), or lens cup frame etc., to frame 12. Thus, referring again to FIG. 2, there is shown hinges 34a to 34b by which lens cups 14a ad 14b are attached to the frame 12. Preferably, these hinges are passive so that the dentist, hygienist, or dental assistant can position the lens cups 14a and 14b snugly against the eye socket as desired. That is, for effective protection of the eye tissue against X-ray radiation a fairly snug fit is required. This is made possible by adjustment or movement of the individual lens cups as shown by directional arrows 36 and 38.

It should be noted, as mentioned previously, that bridge portion 16, having nose pads 40, is located lower than normally found in ordinary spectacles. This is best seen in FIGS. 1 and 3–4. The reason for this is that certain X-ray machines used by dentists i.e., panograph and cephalometric, have a guide portion that rests on the bridge of the nose to stabilize the patient's head during radiography. In order to accomodate use of this type of X-ray machine, the bridge porton 16 is located as shown in the figures.

As is apparent, these features make eye shield 10 ideally suited for use during preparation of dental radiographs. However, eye shield 10 could also be used at any other time it is desired to protect sensitive eye tissue from X-ray or other types of radiation.

While the article herein described constitutes a preferred embodiment of the invention, it is to be understood that the invention is not limited to this precise article, and that changes may be made therein without departing from the scope of the invention.

What is clamed is:

1. An X-ray eye shield for use during dental radiography comprising a radiolucent frame adapted to fit the contours of the head and two radiopaque lens cups attached to said frame in a manner which will bring the lens cups into conformity over the eye sockets when the shield is placed on the head of the patient, said lens cups being attached to said frame by passive hinges which permit adjustment of said lens cups into conformity over the eye sockets after the frame has been placed on the head of the patient, and being made of a material which effectively prevents passage of X-ray radiation, but X-ray radiation otherwise not being occluded by said eye shield so that the important anatomical landmarks necessary for accurate dental diagnosis may be X-rayed without distortion.

2. An X-ray eye shield as set forth in claim 1 wherein said frame is made of a plastic material.

3. An X-ray eye shield as set forth in claim 2 wherein said lens cups are made of 0.030 – 0.040 inch thick lead encased in plastic.

4. An X-ray eye shield as set forth in clam 3 wherein said frames have spring-loaded hinges coextensive with said lens cups.

5. An X-ray eye shield as set forth in claim 2 wherein said frame includes a bridge portion positioned so as not to interfere with use of X-ray machines having a nose guide.

* * * * *